United States Patent [19]

Mitchell et al.

[11] Patent Number: 5,639,916
[45] Date of Patent: Jun. 17, 1997

[54] AMINATION OF ALLYLIC ALCOHOLS

[75] Inventors: John William Mitchell, Wescosville; Gamini Ananda Vedage, Bethlehem, both of Pa.

[73] Assignee: Air Products and Chemicals, Inc., Allentown, Pa.

[21] Appl. No.: 564,666

[22] Filed: Nov. 29, 1995

[51] Int. Cl.$^6$ ............................................. C07C 209/16
[52] U.S. Cl. ............................................................ 564/479
[58] Field of Search ........................... 564/479, 471, 564/474, 480, 503

[56] References Cited

U.S. PATENT DOCUMENTS

| | | | |
|---|---|---|---|
| 2,216,548 | 10/1940 | Converse | 260/585 |
| 3,175,009 | 3/1965 | Koski et al. | 260/585 |
| 4,394,524 | 7/1983 | Ford et al. | 564/479 |
| 4,417,074 | 11/1983 | Daughenbaugh et al. | 564/479 |
| 4,605,770 | 8/1986 | Ford et al. | 564/479 |
| 4,983,736 | 1/1991 | Doumaux, Jr. et al. | 544/402 |

*Primary Examiner*—Brian M. Burn
*Attorney, Agent, or Firm*—Russell L. Brewer; William F. Marsh

[57] ABSTRACT

This invention relates to an improvement in a process for the catalytic amination of an allylic alcohol of the formula:

$$CH_2=CR-CH_2OH$$

where R is hydrogen or methyl with ammonia or an amine of the formula $R_1R_2NH$ where $R_1$ and $R_2$ represent hydrogen or a $C_{1-5}$ hydrocarbyl group in the presence of an effective amount of a phosphorous containing catalyst to effect reaction between the allylic alcohol and the ammonia or amine to produce an allylic amine. The improvement in the process resides in utilizing a neutral group IIA metal phosphate as a catalyst component. Calcium phosphate is preferred and the catalyst.

7 Claims, No Drawings

AMINATION OF ALLYLIC ALCOHOLS

TECHNICAL FIELD OF THE INVENTION

This invention relates to a process for the synthesis of allyl amines by the catalytic amination of allyl alcohols.

BACKGROUND OF THE INVENTION

Allylamine is a polymerizable amine which is well suited for the production of amine functional polymers. Some examples of its use are in the preparation of ion-exchange resins, preparation of polymeric paper additives for enhancing wet and dry strength in paper and the like. Current processes for production of these allylic amines are limited in practical conversion due to observed allylic alcohol polymerization at higher temperatures.

One of the classic routes to the production of allylic amines is by the reaction of allyl halide with ammonia or an amine. The reaction may take place either in the vapor or liquid phases. U.S. Pat. Nos. 2,216,548 and 3,175,009, provide exemplary process descriptions.

U.S. Pat. No. 4,417,074 discloses a process for the generation of allylic amines by the reaction of an allylic alcohol with ammonia or an organic amine in the presence of an effective amount of a phosphorous containing substance. Representative phosphoric containing compositions suited as catalysts include acidic metal phosphates such as boron phosphates, ferric phosphate, aluminum phosphate, phosphoric acid compounds, such as orthophosphoric acid, pyrophosphoric acid and alkyl and aryl substituted phosphorous and phosphoric acids such as methylphosphinic acid and so forth. For an orthophosphoric acid on silica catalyst, '074 shows a 11–23% conversion of allyl alcohol with ammonia at 81% selectivity to monoallylamine. Conditions were 300 psig and 277° to about 320° C.

A variety of amines have been prepared by the reaction of an alkyleneamine and a polyamine to produce alkylene amines such as triethylenetetramine and the like. Phosphorous catalysts have been widely used for the condensation reaction between the alkyleneamine and alkanolamine utilized in the reaction system. U.S. Pat. Nos. 4,983,736; 4,394,524; 4,605,770 are representative. The '770 patent discloses the use of metal acid phosphates including Group IIA and Group IIIB metal phosphates. Group IIA metals suggested include beryllium, magnesium, calcium, strontium, and barium. Group IIIB metals of which lanthanum is a preferred metal included scandium, yttrium and others as the rare earth lanthanide series.

SUMMARY OF THE INVENTION

Broadly, this invention relates to an improved process for producing allylic amines by contacting an allylic alcohol of the formula:

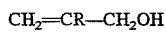

where R is hydrogen or methyl with ammonia or organic amine of the formula $R_1R_2NH$ where $R_1$ and $R_2$ represent hydrogen or a $C_{1-6}$ hydrocarbyl group in the presence of an effective amount of a select phosphorous containing catalyst to effect reaction between the allylic alcohol and ammonia or amine. The improvement in the process resides in utilizing relatively neutral Group IIA metal phosphate compounds selected form the group consisting of calcium, strontium and barium as a catalytic component. Calcium phosphate compounds which are prepared by reacting a calcium salt with a phosphoric acid salt or phosphoric acid itself, are particularly effective as a catalytic component. Neutral catalysts are those having an absorption value equal to those calcium phosphate catalysts having a calcium to phosphorous ratio of from about 1.5 to 2:1

Some of the significant advantages associated with the utilization of the calcium phosphorous catalyst is that higher conversions of allylic alcohol can be achieved e.g. conversions from 55 to about 90% with high selectivity to allylic amines and diallylic amines without affecting the formation of substantial levels of polymeric alcohols and other byproducts.

DETAILED DESCRIPTION OF THE INVENTION

The invention relates to an improved process for synthesizing allylic amines, particularly allylamine and diallyl amine, by the catalytic amination of the precursor alcohol with ammonia or a primary or secondary amine of the formula $R_1R_2NH$ where $R_1$ and $R_2$ represents hydrogen, a $C_{1-6}$ alkyl group, a cycloalkyl group such as cyclohexyl or heterocyclic as in morpholine. Particularly advantageous in the reaction are the methylamines such as monomethylamine and dimethylamine. Other alkyl amines which can be used in generating the allylic amines include mono and di-ethylamine, mono and di-n-propylamine, mono and di-isopropylamine, mono and di-butylamine, isobutylamine, mono and di-n-pentamine and mono and di-cyclohexylamine.

It has been found that although the condensation of the hydroxy group with the amine hydrogen which occurs during amination is enhanced by the acidity of the catalyst, polymerization of the reactant allylic alcohol, and therefore, resultant byproduct formation, is also affected by the acid strength of the catalyst and the support. For example, in amination reactions involving an alkanolamine and an alkyleneamine, a highly acidic phosphorous containing catalyst such as orthophosphoric acid on silica and highly acidic metal acid phosphates such as lanthanum hydrogen phosphate are well suited as catalysts for the reaction. These highly acidic catalysts, however, are not without problems when used in the amination of allylic alcohols.

The catalyst utilized in producing the allylic amines with reduced byproduct formation is a group IIA metal phosphate where the metal is selected from the group consisting of calcium, strontium and barium phosphorous oxides having essentially a neutral acidity. Control of the acidity of the catalyst is key in obtaining amination of the allylic alcohol with enhanced conversion and without substantial byproduct formation. The catalyst typically is a mixture of calcium phosphate and calcium mono and dihydrogen phosphate. The neutrality of the catalyst can be measured by an ammonia neutralization process at atmospheric pressure. The catalyst should have the same neutrality as a calcium phosphate catalyst having a mole ratio of phosphorous ratio of from about 1.5 to 2:1 moles calcium to phosphorous.

A typical procedure for preparing the calcium/phosphorous catalysts first involves dissolving a calcium hydrate salt in deionized (DI) water to a dilute solution. The solution is then pH adjusted with a basic solution such as $NH_4OH$. A second solution of an ammonium phosphate salt is prepared in DI water and the pH adjusted using $NH_4OH$. The phosphate solution is slowly added to the calcium salt solution at moderate temperature 20° to 25° C. in a stirred environment. The formed white precipitate is filtered, washed, and dried in a nitrogen environment at moderate temperatures. The dried material then is pelletized and classified. Acidity, as noted previously, is primarily controlled by adjusting the calcium to phosphorus ratio of the solutions. Calcium to phosphorous ratios (Ca/P) of 1:5 to 2:1 are used with preferred ratios being from about 1.5 to 1.8:1 calcium to phosphorous.

The amination reaction may take place as a gas phase reaction or liquid phase reaction at temperatures ranging from about 100° to 350° C., typically, from 280° to 330° C. The process also can be carried out using batch or continuous processes using conventional techniques and processing apparatus. Pressures typically will range from about 1 to 100 atmospheres, typically 5 to 20 atmospheres. Higher conversions are obtained when the reaction temperature is from about 300° to 330° C. and are preferred for such reaction. Lower temperatures often result in reduced conversion. The mole ratio of ammonia or amine compound to allylic alcohol typically ranges from about stoichiometric to an excess of amine e.g. a molar ratio of from about 1 to 20:1 moles amine per mole alcohol. Catalyst levels are conventional for batch process and conventional LHSV ranges are used in continuous processes. Recovery of the allylic amine products from the reaction mixture can be accomplished by conventional techniques as for example fractional distillation.

The following examples are provided to illustrate various embodiments of the invention and are not intended to restrict the scope thereof.

COMPARATIVE EXAMPLE 1

Amination of Allyl Alcohol with Dimethylamine Over Phosphoric Acid on Silica Catalyst The general procedure of U.S. Pat. No. 4,417,074 was used for the amination of allyl alcohol (AOH) with dimethylamine (DMA) over a phosphoric acid on silica catalyst. More particularly, though, 10 cc of a 34 weight percent phosphoric acid on silica catalyst was charged to the fixed bed tubular reactor, which contained a 10 cc quartz preheat bed. The reactor was heated to a preselected temperature with a resistance heater. Allyl alcohol (AOH) was fed to the reactor, via a constant flow syringe pump, at a liquid hourly space velocity 0.5 per hour. Dimethylamine (DMA) was co-fed to the reactor at a DMA/AOH molar ratio of 4/1. The reactor pressure was maintained at 250 psig by means of a back pressure controller. Effluent from the reactor was continually analyzed by gas chromatography (GC). After several GC samples, the composition of the mixture remained unchanged over time. Table 1 sets forth the reaction conditions and analytical results.

TABLE 1

| Temperature °C. | AOH Conversion % | Selectivity to ADMA % |
| --- | --- | --- |
| 220 | 2.7 | 100.0 |
| 235 | 13.1 | 96.1 |
| 255 | 21.0 | 91.1 |
| 275 | 37.1 | 84.5 |
| 300 | 52.1 | 73.9 |

From the data in Table 1, it appears that allyldimethylamine (ADMA) formation begins at 220° C., (2.7% conversion) with a conversion/selectivity tradeoff being evident at higher temperatures. Above 250° C., the ADMA selectivity starts to fall off below 90%. At temperatures exceeding 300° C. significant AOH polymerization, manifested by severe reactor plugging, is observed. This limits practical reaction conversion to less than about 50% based upon allyl alcohol.

COMPARATIVE EXAMPLE 2

Amination of Allyl Alcohol with Dimethylamine Over Phosphoric Acid on Titania/Alumina Catalyst The procedure of Example 1 was followed except the catalyst 10 cc of a 34% phosphoric acid on titania/alumina catalyst was charged to the fixed bed tubular reactor. The final alcohol conversion is found to be 47.6% at an operating temperature of 300° C., while the alcohol selectivity to allyldimethylamine(ADMA) is measured as 52.2%. These results show that the more acidic support has a slightly detrimental effect as compared to the alumina support.

COMPARATIVE EXAMPLE 3

Amination of Allyl Alcohol with Dimethylamine Over Phosphoric Acid on an LZM-8 Y Type Zeolite The procedure of Example 1 was followed except 10 cc of a 34% phosphoric acid on an LZM-8 Y type zeolite catalyst was tested under these conditions. The results showed a conversion of only 14.8% and a selectivity of 32.6% at an operating temperature of 300° C. These phosphoric acid catalysts show low conversion and selectivity, and if driven to high conversion through the utilization of high temperatures tend to promote allyl alcohol polymerization at high conversions as was the case in Example 1.

COMPARATIVE EXAMPLE 4

Amination of Allyl Alcohol with Dimethylamine Over Boron Phosphate and Other Acid Catalysts The procedure of Example 1 was followed except 10 cc of a Boron Phosphate catalyst and other acidic phosphate catalysts were substituted for the phosphoric acid on silica catalyst. The catalysts were comprised of a mixture of phosphoric acid salts. The effectiveness of the catalysts was evaluated over a wide temperature range. Table 2 sets forth the conditions and results.

TABLE 2

| Catalyst Mixtures | Temp. °C. | AOH Conversion, wt % | ADMA Selectivity, wt % | Comments |
| --- | --- | --- | --- | --- |
| Boron Phosphate | 330 | — | — | Reactor plugged |
| Lanthanum Phosphate | 350 | 0.0 | 0.0 | |
| Strontium hydrogen phosphate | 330 | 45.9 | 95.4 | |
| Zirconium phosphate on alumina | 330 | 56.8 | 41.7 | |
| Lithium phosphate on alumina | 330 | 56.7 | 41.2 | |

The results show conversions equal to those of where phosphoric acid was used in the prior examples, but selectivities were much lower, except for strontium hydrogen phosphate. In all cases the conversion/selectivity was lower than the optimal calcium phosphate catalyst described in Example 6 which follows.

EXAMPLE 5

Calcium Phosphorous Catalyst Preparation

A first solution of 177.2 g of $Ca(NO_3)_2 \cdot 4H_2O$ was dissolved in DI water and diluted to 1 liter. The pH of the first solution was adjusted to 10.5 with aqueous $NH_4OH$ solution. A second solution of 33.0 g of $(NH_4)_2HPO_4$ was dissolved in DI water and diluted to 1 liter. The pH of the second solution was adjusted to 10.5 with NH₄OH solution. Then, 0.6 liter of the Ca(NO₃)₂ first solution was placed In a 5 liter round bottom flask. In a span of 2 minutes 1.5 liter of (NH₄)₂HPO₄ second solution was added with constant stirring. A white precipitate formed. This was filtered after 10 minutes, and washed 3 times. The resultant material was dried in an oven at 110° C. overnight. The dried material was pelletized and classified to +12/−18 mesh, and stored for use in the synthesis reaction. The catalysts were comprised of a mixture of phosphoric acid salts, e.g., calcium phosphate, calcium mono and di hydrogen phosphate and other calcium oxides. The overall Ca/P ratio of the catalyst was 1.7.

Additional calcium phosphate catalysts using various calcium precursor salts, having varying Ca/P ratios, were prepared in a manner similar to that described above.

EXAMPLE 6

Amination of Allyl Alcohol with Dimethylamine Over Calcium/Phosphorous Catalysts The procedure of Example 1 was followed except the catalysts of Example 5 were substituted for the phosphoric acid on silica catalyst. The effectiveness of the catalysts was evaluated over a wide temperature range. Table 3 sets forth the conditions and results.

TABLE 3

| Catalyst | Salt Precursor | Temp. °C. | AOH Conversion, wt % | ADMA Selectivity, wt % |
|---|---|---|---|---|
| Ca/P 1:1 | Calcium nitrate | 330 | 14.7 | 57.3 |
| Ca/P 1.5:1 | Calcium nitrate | 330 | 87.9 | 82.7 |
| Ca/P 1.7:1 | Calcium nitrate | 250 | 32.0 | 96.9 |
| Ca/P 1.7:1 | Calcium nitrate | 300 | 49.7 | 98.0 |
| Ca/P 1.7:1 | Calcium nitrate | 330 | 82.2 | 91.4 |
| Ca/P 2.5:1 | Calcium nitrate | 350 | 36.7 | 0.0 |
| Ca/P 1.7:1 | Calcium acetate | 330 | 87.9 | 96.8 |
| Ca/P 1.7:1 | Commercial | 330 | 77.9 | 96.4 |

From the above Table 3, it is clear that the most active/selective catalyst is the one with a Ca/P ratio of 1.7 Lower Ca/P ratio catalysts gave lower conversions, while those with ratios above 2.0 were not selective to ADMA synthesis at all. Two additional 1.7 Ca/P catalysts were prepared; one as in Example 5, but from calcium acetate,a second from a commercial hydroxyapatite material. Both showed excellent conversion and selectivity, regardless of preparation method. The optimal catalyst was tested as above at a series of temperatures, from 250° to 330° C., as shown in Table 3. In this temperature range as the activity increased, the selectivity to ADMA remained high, e.g., above 90%. The alcohol conversion at 330° C. was found to be 82.2%, while the alcohol selectivity to allyldimethylamine (ADMA) was measured as 91.4%.

These catalysts show improved conversion/selectivity performance with respect to acidic phosphate catalysts studied previously. Only the strontium hydrogen phosphate catalyst was comparable in terms of selectivity but conversions were much less. The 1.7 Ca/P catalyst shows enhanced selectivity compared to the 1.5 Ca/P catalyst, presumably due to lower acid strength. No polymerization was observed for these catalysts over the temperature range studied, allowing for much higher practical conversions.

EXAMPLE 7

Amination of Allyl Alcohol with Monomethylamine Over Calcium/Phosphorous Catalyst 10 cc of the 1.7 Ca/P catalyst described in Example 6 above was charged to a fixed bed tubular reactor, which contains a 10 cc quartz preheat bed. The reactor was heated to 330° C. with a resistance heater. Allyl alcohol (AOH) was fed to the reactor, via a constant flow syringe pump, at a liquid hourly space velocity 0.5 per hour. Monomethylamine (MMA) was co-fed to the reactor at a MMA/AOH molar ratio of 4/1. The reactor pressure was maintained at 250 psig by means of a back pressure controller. Effluent from the reactor was continually analyzed by gas chromatography (GC). After several GC samples, the composition of the mixture remains unchanged over time. The final alcohol conversion was found to be 67.0%, while the alcohol selectivity to N-methylallylamine(NMAA) was measured as 70.5%.

What is claimed is:

1. In a process for the catalytic amination of an allylic alcohol of the formula:

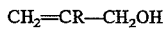

$$CH_2=CR-CH_2OH$$

where R is hydrogen or methyl with ammonia or an amine of the formula $R_1R_2NH$ where $R_1$ and $R_2$ represent hydrogen or a $C_{1-6}$ alkyl or cycloalkyl group in the presence of an effective amount of a phosphorous containing catalyst to effect reaction between the allylic alcohol and the ammonia or amine to produce an allylic amine, the improvement in the process which resides in effecting said catalytic amination in the presence of a neutral Group IIA metal phosphate catalyst component wherein the metals are selected form the group consisting of calcium, strontium and barium.

2. The process of claim 1 where R is hydrogen.

3. The process of claim 2 where $R_1$ is methyl or ethyl.

4. The process of claim 3 where $R_2$ is methyl or ethyl.

5. The process of claim 2 wherein the metal is calcium.

6. The process of claim 5 wherein the mole ratio of calcium to phosphorous in said calcium phosphate catalyst is from about 1.5 to 2:1.

7. The process of claim 6 wherein the mole ratio of calcium to phosphorous is from about 1.5 to 1.8.

* * * * *